US011692951B2

(12) United States Patent
Davis et al.

(10) Patent No.: US 11,692,951 B2
(45) Date of Patent: Jul. 4, 2023

(54) SYSTEM AND METHOD FOR SPECIMEN IMAGING USING AN EXISTING MAMMOGRAPHY IMAGING SYSTEM

(71) Applicant: GE PRECISION HEALTHCARE LLC, Wauwatosa, WI (US)

(72) Inventors: Cynthia Elizabeth Landberg Davis, Niskayuna, NY (US); Paul Francis Fitzgerald, Schenectady, NY (US); Sholom Michael Ackelsberg, Saratoga Springs, NY (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 137 days.

(21) Appl. No.: 17/183,498

(22) Filed: Feb. 24, 2021

(65) Prior Publication Data

US 2022/0265229 A1    Aug. 25, 2022

(51) Int. Cl.
*G01N 23/044* (2018.01)
*A61B 6/04* (2006.01)

(52) U.S. Cl.
CPC .......... *G01N 23/044* (2018.02); *A61B 6/0414* (2013.01)

(58) Field of Classification Search
CPC ............... G01N 23/044; G01N 23/046; G01N 2223/6126; G01N 33/4833; A61B 6/502; A61B 6/025; A61B 6/466; A61B 6/0414
See application file for complete search history.

(56) References Cited

U.S. PATENT DOCUMENTS

| 5,023,895 | A | 6/1991 | McCroskey et al. |
| 5,383,234 | A * | 1/1995 | Russell .................... H05G 1/26 378/208 |
| 8,503,602 | B2 * | 8/2013 | Lafferty ............. A61B 10/0096 378/37 |
| 9,138,193 | B2 | 9/2015 | Lowe et al. |
| 9,750,484 | B2 * | 9/2017 | Finke .................... A61B 5/061 |
| 10,322,412 | B2 | 6/2019 | Purdy et al. |
| 10,542,951 | B2 * | 1/2020 | Klausz ................ A61B 6/0414 |
| 2010/0080346 | A1 | 4/2010 | Kalender et al. |
| 2010/0191145 | A1 * | 7/2010 | Lafferty ................. A61B 90/11 378/189 |

(Continued)

OTHER PUBLICATIONS

Miller, Cynthia L., et al.; "Comparison of Intra-Operative Specimen Mammography to Standard Specimen Mammography for Excision of Non-Palpable Breast Lesions: A Randomized Trial", Breast Cancer Res. Treat (2016), pp. 513-519.

(Continued)

*Primary Examiner* — Dani Fox
*Assistant Examiner* — Soorena Kefayati
(74) *Attorney, Agent, or Firm* — Fletcher Yoder P.C.

(57) ABSTRACT

An intraoperative specimen imaging system is provided. The intraoperative specimen imaging system includes a mammography imaging system configured to acquire imaging data. The intraoperative specimen imaging system also includes a specimen holding system configured to hold a tissue sample, wherein the specimen holding system is retrofittedly coupled to the mammography imaging system, wherein the intraoperative specimen imaging system is configured to acquire imaging data for generating three-dimensional (3D) images of the tissue sample.

17 Claims, 6 Drawing Sheets

(56) References Cited

U.S. PATENT DOCUMENTS

| | | | |
|---|---|---|---|
| 2011/0021947 A1* | 1/2011 | Nakayama | A61B 6/469 |
| | | | 378/37 |
| 2012/0238870 A1* | 9/2012 | Smith | A61B 6/466 |
| | | | 600/431 |
| 2013/0259193 A1* | 10/2013 | Packard | A61B 6/502 |
| | | | 378/37 |
| 2015/0327826 A1 | 11/2015 | Smith et al. | |
| 2016/0310215 A1* | 10/2016 | Palma | A61B 34/10 |
| 2017/0020473 A1* | 1/2017 | Klausz | A61B 6/5205 |
| 2017/0082557 A1* | 3/2017 | Iordache | A61B 6/502 |
| 2017/0105709 A1* | 4/2017 | Ellis | A61B 90/92 |
| 2017/0138870 A1 | 5/2017 | Buijsse et al. | |
| 2017/0245810 A1* | 8/2017 | Maidment | A61B 6/025 |
| 2017/0265828 A1* | 9/2017 | Tsujii | A61B 5/0091 |
| 2017/0336706 A1* | 11/2017 | Wang | A61B 6/032 |
| 2018/0168523 A1* | 6/2018 | Vancamberg | A61B 10/0233 |
| 2019/0231323 A1* | 8/2019 | Gollwitzer | A61B 10/0233 |
| 2019/0285558 A1* | 9/2019 | Defreitas | G01N 23/087 |

OTHER PUBLICATIONS

Park, Ko Un, M.D., et al.; "Digital Breast Tomosynthesis for Intraoperative Margin Assessment During Breast-Conserving Surgery", Annals of Surgical Oncology (2019), pp. 1720-1728.

Lee et al., "A fit-panel detector based micro-CT system: performance evaluation for small-animal imaging," Physics in Medicine and Biology, vol. 48, 2003, 14 pgs.

France Application No. 2200935, Preliminary Search Report, dated May 24, 2023, 11 pgs.

* cited by examiner

SYSTEM AND METHOD FOR SPECIMEN IMAGING USING AN EXISTING MAMMOGRAPHY IMAGING SYSTEM

BACKGROUND

The subject matter disclosed herein relates to specimen imaging and, more particularly, utilizing an existing mammography imaging system for specimen imaging.

In breast lumpectomy surgery, a surgeon's objective is to remove the tumor while conserving as much healthy breast tissue as possible. In striving for the latter, tumor tissue is sometimes left behind in the breast, or the distance between the tumor and the boundary of the lumpectomy specimen is too small (i.e., positive margins). In the case of positive margins, additional surgery (re-excision) is often performed, at additional trauma and risk to the patient, as well as additional cost. The frequency of re-excision depends on the institution and the surgeon, ranging from 10 percent (for expert surgeons at institutions that perform many lumpectomies) to 50 percent or higher (for surgeons with far less experience at smaller institutions). The current standard of care is to evaluate for positive margins using histopathology, which takes more than a day before results are available. In some institutions, intra-operative lumpectomy evaluation is performed using various approaches with various levels of effectiveness. For example, two-dimensional (2D) specimen evaluation can be performed using a commercial "cabinet" imaging system in the operating room or by sending the specimen to the radiology department to be imaged on a mammography imaging system. However, neither of these solutions provides enough information to confidently detect or to rule out positive margins. In addition, sending the specimen to the radiology department introduces delay and can create scheduling issues. If three-dimensional (3D) information were available during surgery to enable margin assessment that is as good as or better than that provided with histopathology, then the re-excision rate could potentially be reduced to zero. Ideally, the 3D assessment capability would be available in the operating room.

BRIEF DESCRIPTION

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In accordance with an embodiment, an intraoperative specimen imaging system is provided. The intraoperative specimen imaging system includes a mammography imaging system configured to acquire imaging data. The intraoperative specimen imaging system also includes a specimen holding system configured to hold a tissue sample, wherein the specimen holding system is retrofittedly coupled to the mammography imaging system, wherein the intraoperative specimen imaging system is configured to acquire imaging data for generating three-dimensional (3D) images of the tissue sample.

In accordance with another embodiment, a method for intraoperative specimen imaging is provided. The method includes coupling a specimen holding system to a mammography imaging system, wherein the specimen holding system includes a specimen holder, an attachment for coupling the specimen holder to the mammography imaging system, and a motor configured to rotate the specimen holder. The method also includes rotating the specimen holder to rotate a tissue sample to different angular positions over a specific angular range while emitting radiation from a radiation source of the mammography imaging system to acquire imaging data of the tissue sample at the different angular positions. The method further includes generating three-dimensional (3D) images of the tissue sample from the imaging data acquired at different angular positions over the specific angular range.

In accordance with a further embodiment, a specimen holding system is provided. The specimen holding system includes a specimen holder configured to hold a tissue sample, an attachment configured to couple the specimen holder to a mammography imaging system, and a motor configured to rotate the specimen holder. The specimen holding system is configured to retrofittedly couple to the mammography imaging system to form an intraoperative specimen imaging system configured to acquire imaging data of the tissue sample at different angular positions over an angular range of up to at least 360 degrees for generating three-dimensional (3D) images of the tissue sample.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
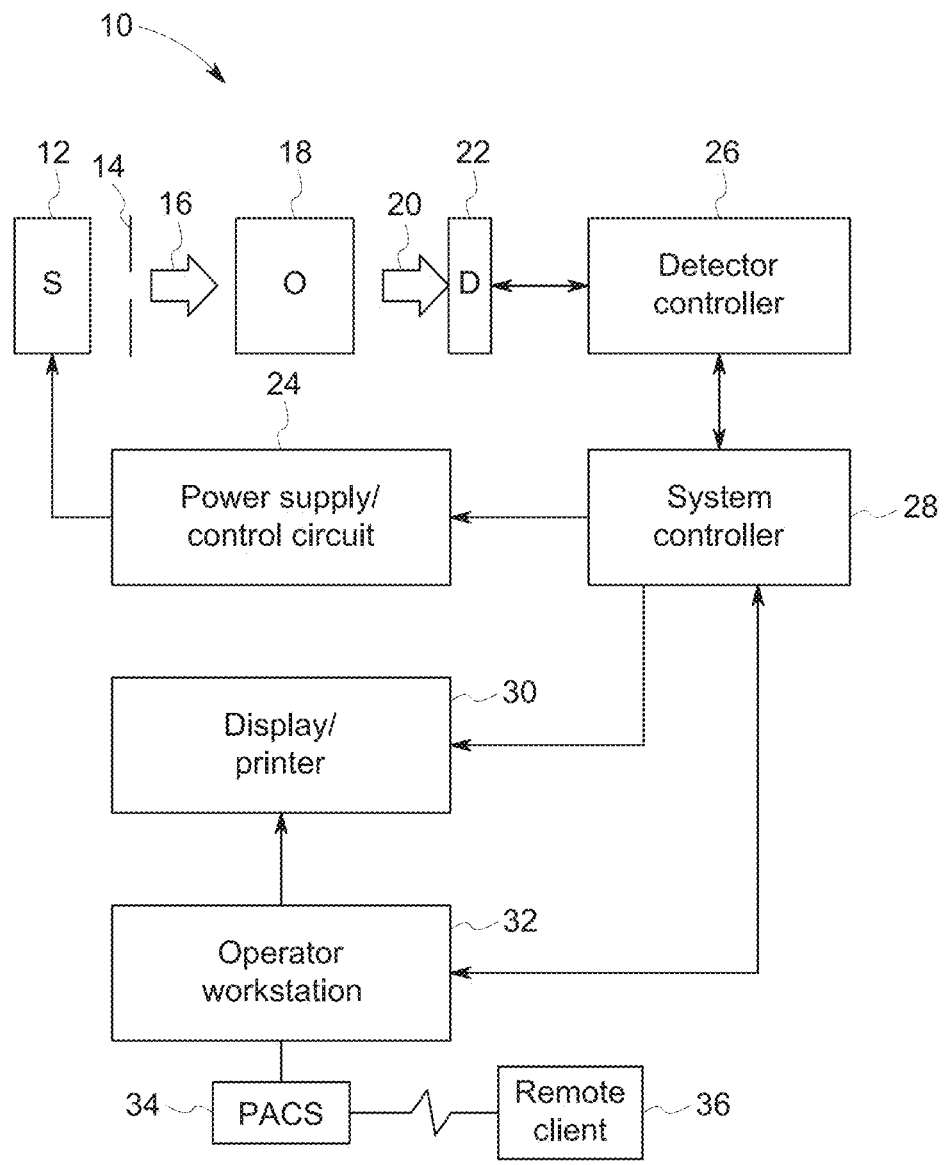
FIG. 1 is an embodiment of a digital X-ray system (e.g., mammography imaging system), in accordance with aspects of the present disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

The present disclosure provides systems and methods for specimen imaging (e.g., intraoperative specimen imaging) utilizing an existing mammography imaging system for specimen imaging. In particular, an intraoperative specimen imaging system includes a specimen holding system configured to hold a tissue sample, wherein the specimen holding system is retrofittedly coupled to an existing mammography imaging system, wherein the intraoperative specimen imaging system is configured to acquire imaging data for generating 3D images of the tissue sample. In certain embodiments, the specimen holding system includes a specimen holder and a motor coupled to the specimen holder that rotates the specimen holder having the tissue sample between exposures. In certain embodiments, the specimen may be rotated continuously. In certain embodiments, the existing mammography imaging system includes a full-field digital mammography imaging system configured to acquire 2D imaging data. In certain embodiments, the existing mammography imaging system includes a digital breast tomosynthesis imaging system that is configured to acquire 2D imaging data (e.g., projection data) over a limited angular range (e.g., 60 degrees or less) for generating 3D imaging data. The intraoperative specimen imaging system may acquire imaging data over an angular range of up to 360 degrees plus an additional angular range to ensure data completeness. In addition, the imaging data may be acquired at a higher resolution due to imaging in a magnification mode. The intraoperative specimen imaging system may be utilized within an operating room during a procedure (e.g., breast lumpectomy surgery, mastectomy, etc.) on a patient from which the tissue sample was taken to provide improved intraoperative imaging (e.g., high resolution 3D images) at lower costs to an institution (which may not normally have intraoperative specimen imaging available).

Turning now to the drawings, FIG. 1 illustrates diagrammatically an imaging system 10 (e.g., mammography imaging system) for acquiring and processing discrete pixel image data. In the illustrated embodiment, system 10 is a digital X-ray system designed both to acquire original image data and to process the image data for display in accordance with the present technique. The imaging system 10 may be a stationary system disposed in a fixed X-ray imaging room or a mobile X-ray system. The imaging system 10 is a mammography imaging system. In certain embodiments, the imaging system 10 is a full-field digital mammography imaging system configured to acquire 2D imaging data. In certain embodiments, the imaging system 10 is a digital breast tomosynthesis imaging system is configured to acquire 2D imaging data (e.g., projection data) over a limited angular range (e.g., 60 degrees or less) for generating 3D imaging data. In particular, the imaging system 10 is an existing mammography imaging system retrofitted with a specimen holding system that enables the 2D imaging data to be acquired of a tissue sample (of a breast or any other tissue type) over an angular range of up to 360 degrees plus an additional angular range to ensure data completeness to enable the generation of 3D images as described in greater detail below.

In the embodiment illustrated in FIG. 1, imaging system 10 includes a source of X-ray radiation 12 positioned adjacent to a collimator 14. Collimator 14 permits a stream of radiation 16 to pass into a region in which an object 18 (e.g., tissue or biopsy sample) is positioned. A portion of the radiation 20 passes through or around the subject and impacts a digital X-ray detector, represented generally at reference numeral 22. In certain embodiments, the detector 22 may convert the X-ray photons incident on its surface to lower energy photons, and subsequently to electric signals, which are acquired and processed to reconstruct an image of the features within the object or subject. In other embodiments, such as in a direct conversion implementation, the incident radiation itself may be measured without an intermediary conversion process.

Source 12 is controlled by a power supply/control circuit 24 which furnishes both power and control signals for examination sequences. Moreover, detector 22 includes a detector controller 26 (e.g., control circuitry) which commands acquisition of the signals generated in the detector 22. Detector controller 26 may also execute various signal processing and filtration functions, such as for initial adjustment of dynamic ranges, interleaving of digital image data, and so forth. Both power supply/control circuit 24 and detector controller 26 are responsive to signals from a system controller 28. In general, system controller 28 commands operation of the imaging system to execute examination protocols and to process acquired image data. In the present context, system controller 28 also includes signal processing circuitry and associated manufactures, such as optical memory devices, magnetic memory devices, or solid-state memory devices, for storing programs and routines executed by a processor to carry out various functionalities (e.g., acquisition of imaging data in magnification mode; reconstruction of imaging data via a cone beam computed tomography (CT) reconstruction such as a back projection, iterative reconstruction, or other reconstruction method; computer aided detection (CAD) module for automatic detection of calcification, markers, and/or mass within a tissue sample; rotation of the tissue sample or specimen via the specimen holding system in synchrony with exposures; adding a post-imaging electronic grid or other fiducials or indicators to an image that indicates a distance and location of a tissue sample relative to the patient from which the sample was taken; and storing configuration parameters, and image data; interface protocols; and so forth). In one embodiment, a programmed computer system may be provided with hardware, circuitry, firmware, and/or software for performing the functions attributed to one or more of the power supply/control circuit 24, the detector controller 26, and/or the system controller 28 as discussed herein.

In certain embodiments, where the imaging system 10 is a digital breast tomosynthesis imaging system, the system controller 28 is coupled to a rotational subsystem. The rotational subsystem enables the X-ray source 12 and collimator 14, to be rotated over a limited angular range (e.g., 60 degrees or less) about the object 18, such as rotated primarily in an x, y-plane about the object 18. It should be noted that the rotational subsystem might include a gantry upon which the respective X-ray emission and detection components are disposed. Thus, in such an embodiment, the system controller 28 may be utilized to operate the gantry.

In the embodiment illustrated in FIG. 1, system controller 28 is linked to at least one output device, such as a display or printer as indicated at reference numeral 30. In certain embodiments, images may be displayed in a video loop (e.g., cinematic mode) on the display for a radiologist or surgeon to view during a procedure (e.g., in the operating room). The output device may include standard or special purpose monitors and associated processing circuitry. In certain embodiments, one or more operator workstations 32 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

It should be further noted that the operator workstation 32 may also be coupled to a picture archiving and communications system (PACS) 34 or other review work station. The PACS 34 may run a Digital Imaging and Communications in Medicine (DICOM) server for generating DICOM images of the tissue sample. PACS 34 may in turn be coupled to a remote client 36, radiology department information system (RIS), hospital information system (HIS) or to an internal or external network, so that others at different locations may gain access to the raw or processed image data.

Figure 2:
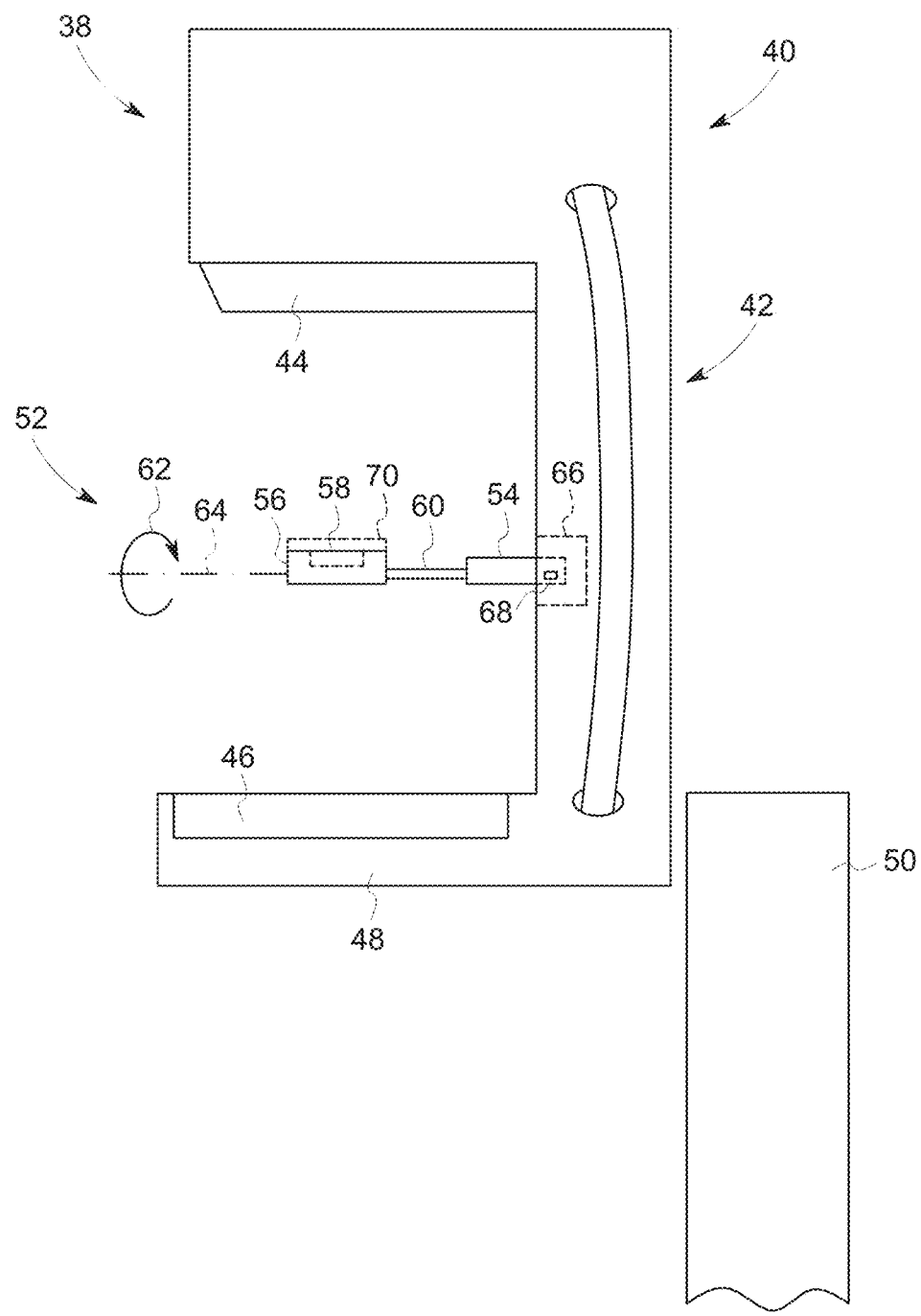
FIG. 2 illustrates an embodiment of an intraoperative imaging system, in accordance with aspects of the present disclosure.

FIG. 2 illustrates an imaging system 38. The imaging system 38 includes an apparatus (e.g., existing mammography imaging system) for mammography imaging 40. The apparatus 40 includes an arm 42, which has a radiation source 44, such as an X-ray tube, at one of its ends, and which, at its other end, has an X-ray detector 48. The end of the arm 42 having the X-ray detector 48 may also include a support device 46, such as a breast support plate to support a breast for mammography imaging, which can be removable if desired. The arm 42 is mounted on a frame 50. In certain embodiments, the radiation source and/or the X-ray detector 46 may be directly coupled to the frame 50. In certain embodiments (e.g., for a digital breast tomosynthesis imaging system as shown in FIGS. 5A, 5B and 6A, 6B), the X-ray tube 44 can be pivoted or rotated over a limited angular range (e.g., 60 degrees or less), particularly around a horizontal axis, for example, while the X-ray detector 46 remains stationary.

As depicted, a specimen holding system 52 is coupled to the apparatus 40. The specimen holding system 52 includes an attachment 54 for coupling the system 52 to the apparatus 40, a specimen holder 56 for holding a tissue sample 58, and a motor-driven mechanism 60 for rotating the specimen holder 56 up to 360 degrees plus an additional angular range for data completeness about an axis 64 (e.g., horizontal axis) as indicated by arrow 62. The specimen holding system 52 provides a greater angular range for acquiring imaging data than a digital breast tomosynthesis imaging system. In certain embodiments (e.g., as shown in FIGS. 5A, 5B and 6A, 6B) where a digital breast tomosynthesis imaging system is utilized, the specimen holding system 52 may not include a motor-driven mechanism but may include a mechanism that couples the specimen holder 56 to the gantry that enables the specimen holder 56 to remain stationary as the radiation source 44 moves. In some embodiments the specimen holder 56 may move as the radiation source 44 moves to keep the projection of the X-ray source and specimen on the X-ray detector 46 and avoid edge effects and cut-off. This enables the digital breast tomosynthesis imaging system to be utilized in a magnification mode when imaging the specimens.

The attachment 54 may be inserted within a receptacle 66 normally configured to receive a compression paddle or magnification stand. In certain embodiments, the insertion of the attachment 54 into the receptacle 66 will cause (or trick) the apparatus 40 to operate in magnification mode (e.g., for geometric magnification>1) as opposed to contact mode (i.e., the mode utilized if a breast was placed in contact with the support device 46). In magnification mode, an object (e.g., the tissue sample) will be closer to the X-ray source and further from the detector. In magnification mode, a geometric magnification may be limited by the configuration of the system to 1.5× to 2×. In certain embodiments, the geometric magnification may be up to 5× or even 10×. In addition, the field of view of the object may be reduced in magnification mode (e.g., for 2×, from 300 mm to 150 mm) and the effective pixel size at the object will be reduced proportionately (e.g., for 2×, from 100 µm to 50 µm). It should be noted that, for magnification mode, the X-ray source's focal spot size may need to be reduced in order to achieve the desired spatial resolution. This may reduce the maximum power of the X-ray source and consequently require a longer scan time and higher radiation dose versus a non-magnified mode; however, because this is a specimen scanner, these are acceptable tradeoffs. This, in conjunction, with no limits on the radiation dose, enables high resolution images of the tissue sample 58. It should be noted that (whether the specimen is rotated or not) it remains within the field of view during the image acquisition.

In certain embodiments, the specimen holding system 52 may include a hardware identifier 68 (e.g., bar code or other readable marker) configured to be scanned or read by the apparatus 40. In certain embodiments, the apparatus 40 may include an optical reader to scan or read the marker 68. In certain embodiments, assuming that the system enables the introduction of new compression paddles and software, scanning or reading of the marker 68 causes a special program to be accessed or obtained (e.g., from memory) by the apparatus 40 for imaging intraoperative imaging of the tissue sample 58 (e.g., in magnification mode). In particular, the apparatus 40 in response to reading the marker 68 causes the apparatus 40 (e.g., automatically) to acquire imaging data at different angular positions (over an angular range of up to at least 360 degrees) with motor-driven mechanism 60 rotating the specimen holder 56 (and the tissue sample 58). The motor-driven mechanism 60 rotates the tissue sample 58 in synchrony with the exposures if in a step and shoot mode.

In certain embodiments, the system may not be open and the marker 68 utilized may be that normally utilized for a spot compression paddle. In some systems without access to controls, a user utilizes a manual mode to set up the acquisition sequence or exposures. In this case, a look up table of suggested exposures may be provided to the user.

As mentioned above, the motor-driven mechanism 60 can rotate the tissue sample 58 over an angular range of up to 360 degrees plus an additional angular range for data completeness. For an image acquisition sequence, between each exposure, the motor-driven mechanism 60 rotates the tissue sample approximately 90 degrees or less. The angular rotation of the tissue sample 58 between exposures may range from approximately 0.1 to 90 degrees. Thus, the number of angular positions at which imaging data may be acquired (and, thus, the number of acquired images) may range from 4 to 3600. In a preferred embodiment the tissue sample will rotate 1 degree per image. In system that allows the control software to be modified, the X-ray trigger may only need to be pressed once (and held) for the image acquisition sequence. In other systems, the X-ray trigger may need to be pressed multiple times during the image acquisition sequence. It should be noted, in certain embodiments, the specimen may be rotated continuously.

In certain embodiments, the specimen holder 56 may include a fiducial 70 (e.g., radio-opaque grid, electronic grid, or any other type of fiducial). The fiducial 70 provides a distance and location for the tissue sample 58 (e.g., via an alpha/numeric grid) in a subject or patient from which the tissue sample 58 was obtained. The fiducial 70 appears on the acquired image. In certain embodiments, via the processing circuitry, an electronic fiducial may be added as a reference post exposure. The information from the fiducial 70 (e.g., distance and location), if provided to the system, enables the image of the tissue sample 58 to be displayed on review relative to its pre-excision orientation and location within the patient. In certain embodiments, a surgeon may place the tissue sample 58 on a localizing fiducial in the operating room.

Figure 3:
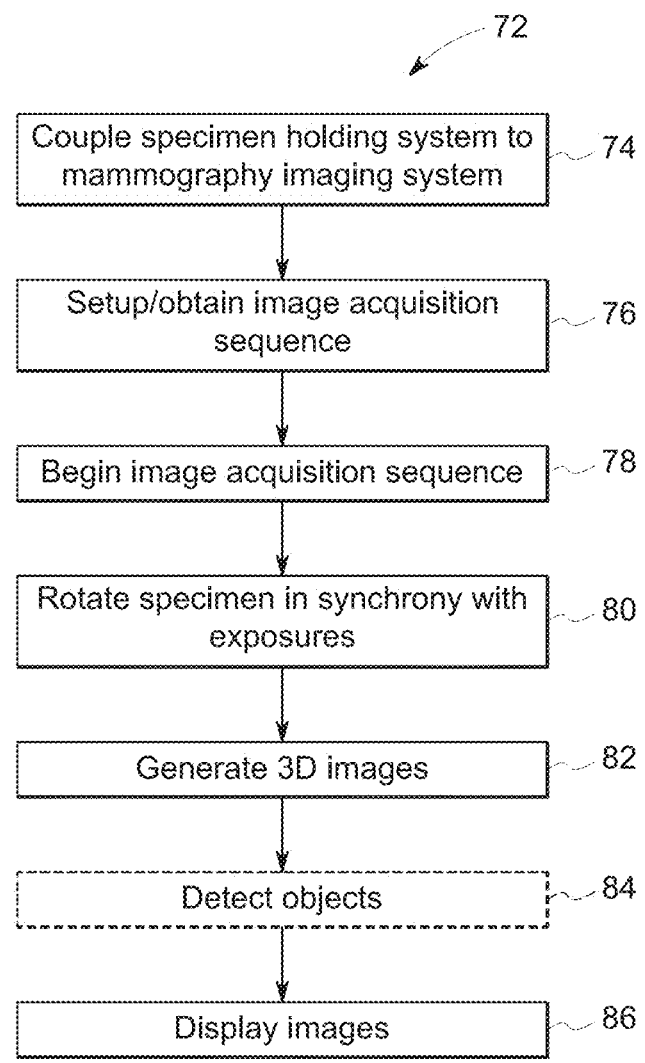
FIG. 3 illustrates a flow chart of an embodiment of a method for intraoperative imaging of a tissue sample, in accordance with aspects of the present disclosure.

FIG. 3 illustrates a flow chart of an embodiment of a method 72 for intraoperative imaging of a tissue sample. One or more steps of the method 72 may be performed by a component of the intraoperative imaging system in FIGS. 1 and 2 or a processor-based system. The method 72 includes coupling a specimen holding system to an existing mammography imaging system (e.g., a digital breast tomosynthesis imaging system or a full-field digital mammography imaging system) (block 74). For example, an attachment of a specimen holding system may be inserted within a receptacle normally configured to receive a compression paddle or magnification stand of the existing mammography imaging system.

The method 72 also includes setting up or obtaining an image acquisition sequence (block 76). In an open system, a marker may be read or scanned on the specimen holding system (e.g., upon coupling of the specimen holding system) that obtains a special program for intraoperative imaging of a tissue sample that has been stored within a memory of the mammography imaging system. In other systems, a user may have to manually setup the imaging system (e.g., utilizing a providing a look up table of suggested exposures).

The method 72 further includes beginning the image acquisition sequence (block 78) (e.g., via pressing of an X-ray trigger). The method 72 even further includes rotating the tissue sample in synchrony with the exposures (block 80). In certain embodiments (e.g., in an open system), the system automatically alternates between an exposure and rotating the tissue sample to a different angular position over the angular range (e.g., up to 360 degrees). In other embodiments, a user may have to manually trigger an exposure between each rotation of the tissue sample. It should be noted, in certain embodiments, the specimen may be rotated continuously.

The method 72 still further includes generating 3D images (block 82) from the imaging data acquired over an angular range of greater than 2 degrees (and up to 360 degrees plus an additional angular range for data completeness). Reconstruction of the imaging data into 3D images may occur via a cone beam computed tomography (CT) reconstruction such as a back projection, iterative reconstruction, and deep-learning based or other reconstruction method. The imaging data may be sent to a process-based system running a DICOM server for reconstruction. In certain embodiments, the method 72 includes detecting objects within the images of the tissue sample (block 84). For example, a CAD module may automatically detect calcifications, markers, and/or mass within the images.

The method 72 also includes displaying the 3D images (block 86). For example, the images may be displayed on a display (e.g., on a work station) in an operating room for viewing by a surgeon or radiologist. In certain embodiments, the images may be displayed on a PACS system in the operating room. In certain embodiments, the images may be displayed in a video loop (e.g., Cine mode) on a display in the operating room. The images may include grid or other fiducial information related to distance as well as location relative to the location and orientation of the specimen before excision from the patient. As mentioned above, this information may be provided to the system to enable a sketch of the patient and an orientation of the specimen image to be displayed in the review.

Figure 4:
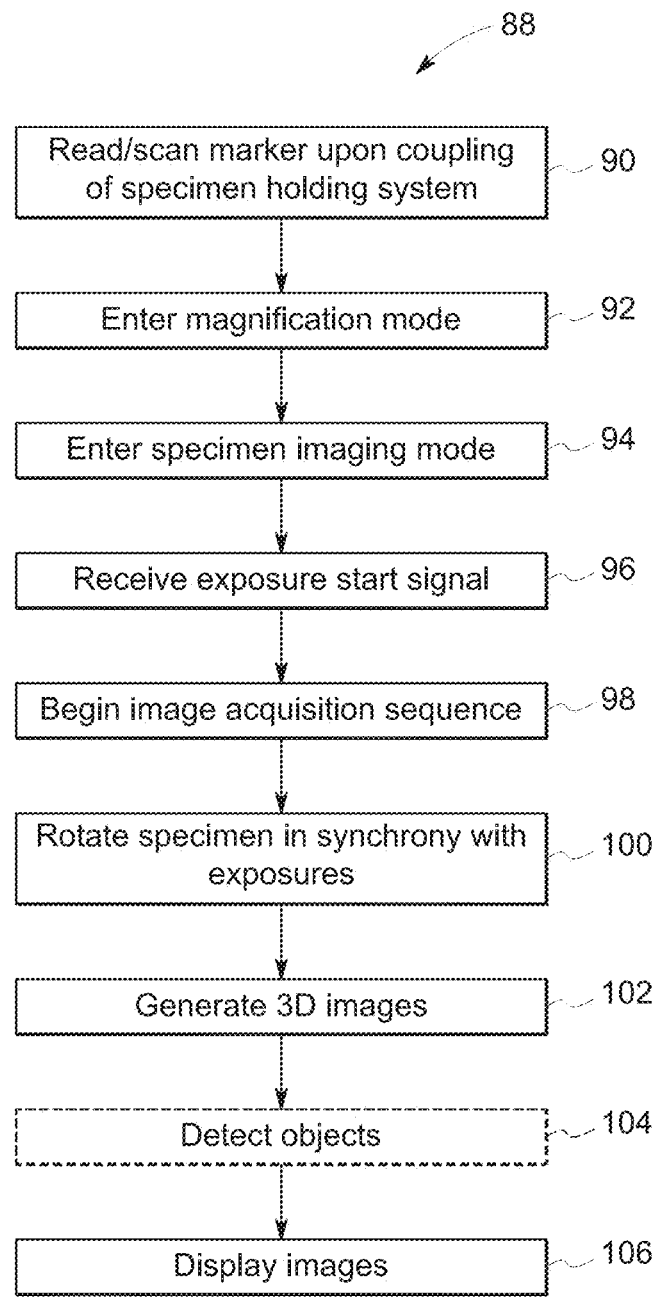
FIG. 4 illustrates a flow chart of an embodiment of another method for intraoperative imaging of a tissue sample, in accordance with aspects of the present disclosure.

FIG. 4 illustrates a flow chart of an embodiment of a method 88 for intraoperative imaging of a tissue sample. One or more steps of the method 88 may be performed by a component of the intraoperative imaging system in FIGS. 1 and 2 or a processor-based system. One or more of the steps in the method 88 may be performed in a different order or simultaneously. The method 88 includes reading or scanning a marker associated with a specimen-holding system upon coupling the specimen-holding system to an existing mammography imaging system (e.g., a digital breast tomosynthesis imaging system or a full-field digital mammography imaging system) (block 90). For example, an attachment of a specimen-holding system may be inserted within a receptacle normally configured to receive a compression paddle or magnification stand of the existing mammography imaging system. The method 88 includes entering magnification mode (block 92) and specimen imaging mode (e.g., intraoperative imaging mode) (block 94) upon reading or scanning the marker. In magnification mode, a geometric magnification of typically up to 1.5× to 2× may be utilized during the image acquisition sequence. Entering specimen imaging mode includes obtaining from the memory of the mammography imaging system a special program for intraoperative imaging of a tissue sample that includes a specific image acquisition sequence. In certain embodiments, a user may be able to select a desired number of images and/or angular range for acquiring the imaging data or select from among different specific image acquisition sequences.

The method 88 further includes beginning the image acquisition sequence (block 96) (e.g., via pressing of an X-ray trigger). The method 88 even further includes rotating the tissue sample in synchrony with the exposures (block 100). The system automatically alternates between an exposure and rotating the tissue sample to a different angular position over the angular range (e.g., up to at least 360 degrees). It should be noted, in certain embodiments, the specimen may be rotated continuously.

The method 88 still further includes generating 3D images (block 102) from the imaging data acquired over an angular range of greater than 60 degrees (and up to 360 degrees). Reconstruction of the imaging data into 3D images may occur via a cone beam computed tomography (CT) reconstruction such as a back projection, iterative reconstruction, or other reconstruction method. The imaging data may be sent to a process-based system running a DICOM server for reconstruction. In certain embodiments, the method 88 includes detecting objects within the images of the tissue sample (block 104). For example, a CAD module may automatically detect calcifications, markers, and/or mass within the images.

The method 88 also includes displaying the 3D images (block 106). For example, the images may be displayed on a display (e.g., on a work station) in an operating room for viewing by a surgeon or radiologist. In certain embodiments, the images may be displayed on a PACS system in the operating room. In certain embodiments, the images may be displayed in a video loop (e.g., Cine mode) on a display in the operating room. The images may include fiducial information related to distance as well as location in a patient. As mentioned above, this information may be provided to the system to enable a sketch of the patient an orientation of the specimen image to be displayed in the review.

Figure 5A:
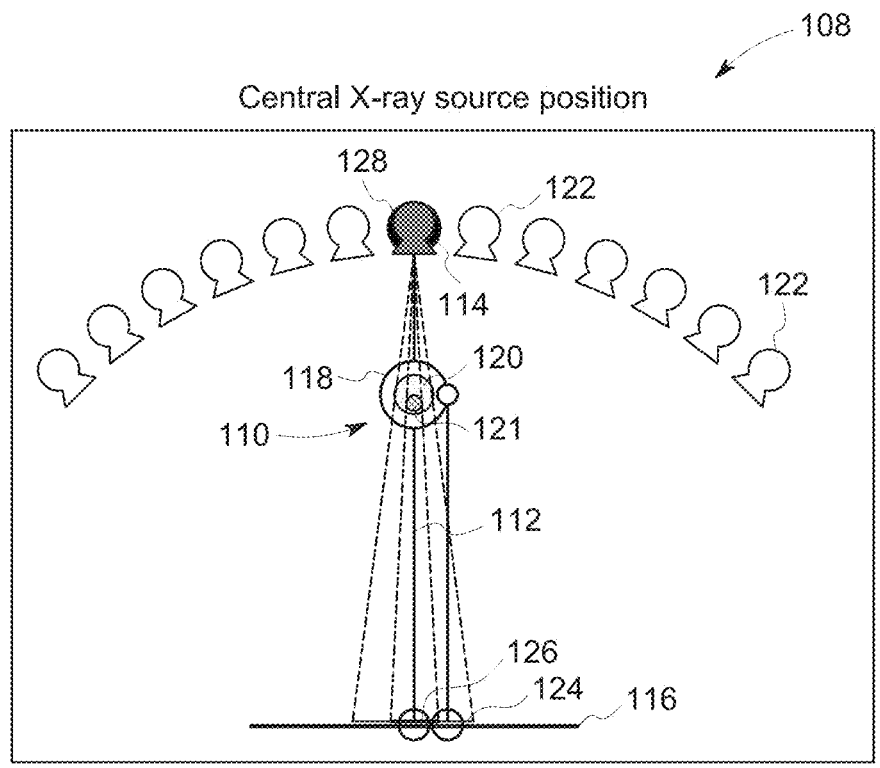
FIGS. 5A and 5B illustrate an embodiment of a digital breast tomosynthesis imaging system modified to operate in a magnification mode for imaging of a specimen (e.g., at high magnification)
Figure 5B:
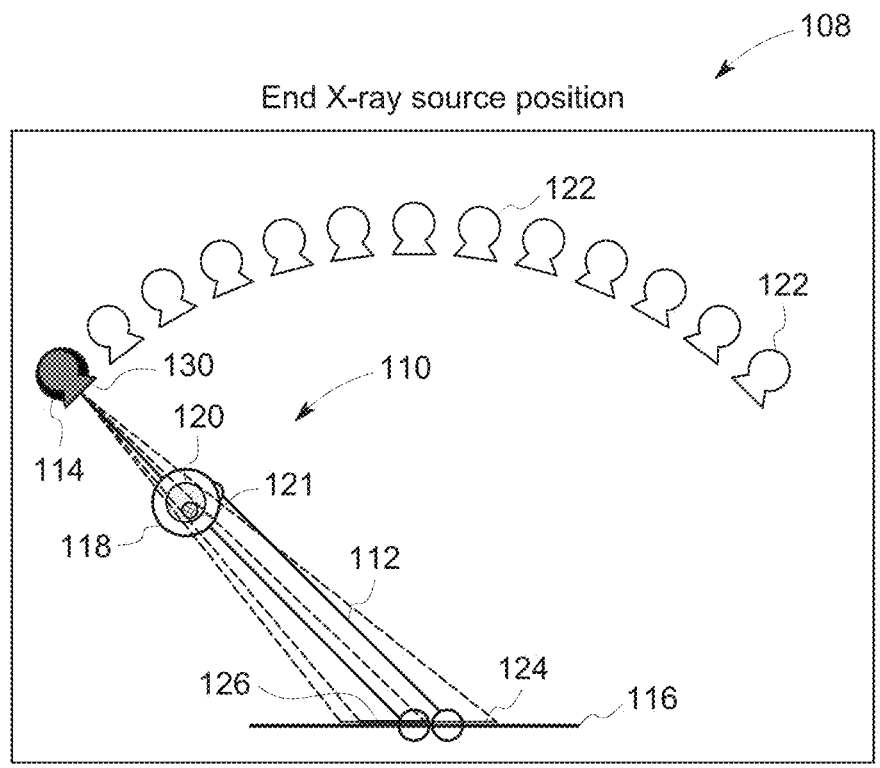
Figure 6A:
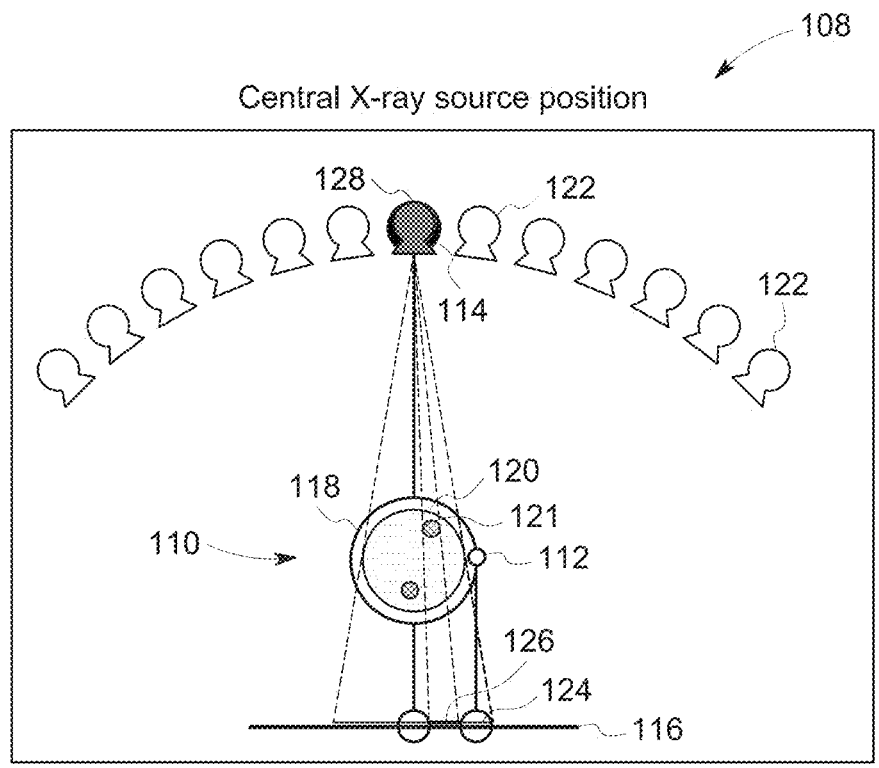
FIGS. 6A and 6B illustrate an embodiment of a digital breast tomosynthesis imaging system modified to operate in a magnification mode for imaging of a specimen (e.g., at low magnification).
Figure 6B:
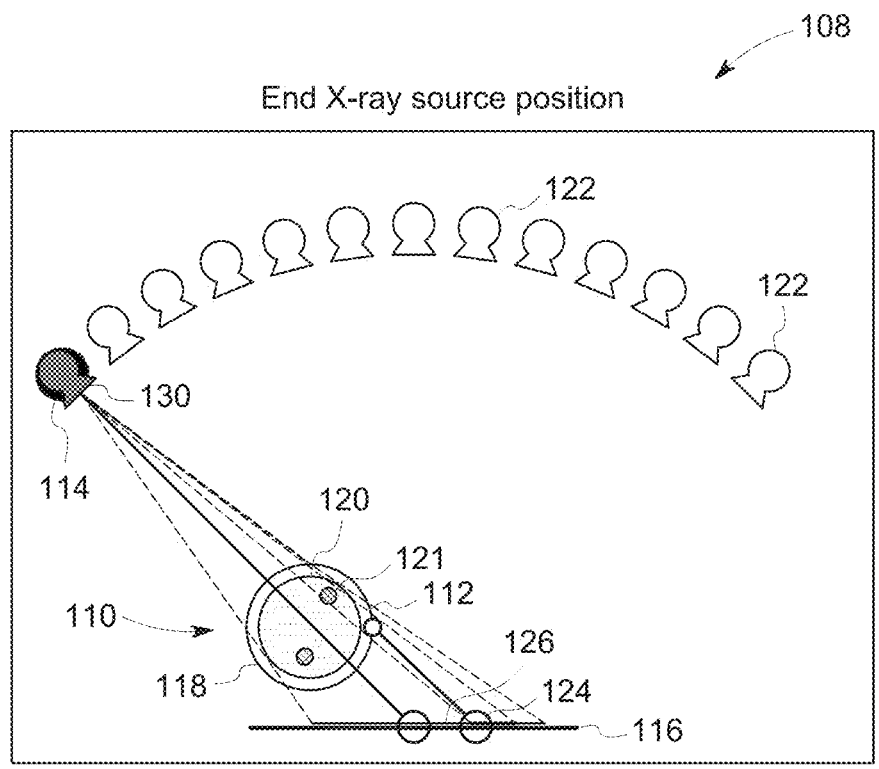

FIGS. 5A and 5B illustrate an embodiment of a digital breast imaging system 108 modified to operate in a magnification mode for imaging of a specimen (e.g., at high magnification). As illustrated, a specimen holding system 110 includes a non-motorized mechanical apparatus 112 (e.g., that utilizes a passive mechanical specimen positioning) attached between the X-ray source 114 (e.g., X-ray tube) and the detector 116 of the digital breast tomosynthesis imaging system 108. The specimen holding system 100 also includes a specimen holder 118 attached to the apparatus that holds the specimen 120 (which includes a feature 121 (e.g., tumor)) at a distance from the detector 116 to enable magnification. As the X-ray source 114 automatically moves to different angular positions 122 between X-ray exposures to acquire projections (e.g., projection 124 of the specimen 120 and projection 126 of the feature 121) over an angular range appropriate for digital tomosynthesis. In doing so, the attached non-motorized apparatus 112 is moved to the same angle as the X-ray source 114, thus positioning the specimen 120 in consistent alignment between the X-ray source 114 and the detector 116, i.e., consistent lateral position relative to the X-ray source and detector, consistent rotational orientation relative to the detector, and at consistent geometric magnification. In FIG. 5A, the position 122 of the X-ray source 114 is a central position 128. In FIG. 5B, the position 122 of the X-ray source 114 is an end position 130. Appropriate geometric calibration and reconstruction are utilized in conjunction with the utilization of the specimen holding system 110 to acquire imaging data for the specimen 120. Typically, the DBT imaging system 108 cannot operate in magnification mode because the projections would miss the detector. However, the specimen holding system 110 in FIGS. 5A and 5B enables the DBT imaging system 108 to operate in magnification mode. FIGS. 6A and 6B illustrates the DBT imaging system 108 modified to operate in a magnification mode for imaging of a specimen similar to FIGS. 5A and 5B except the specimen holding system 100 is configured for lower constant magnification and for holding a larger specimen.

The techniques described above will provide a moderate level of 3D assessment capability to an operating room by retrofitting a preexisting mammography imaging system not capable of acquiring 3D images over a larger angular range (greater than 25 degrees and up to 360 degrees). These high-resolution images may provide enough information to confidently detect or rule out positive margins in a timely manner, which may result in a margin assessment as good as or better than with histopathology, and reduce the need for additional surgery (e.g., re-excision). In certain embodiments, the disclosed techniques may help locate tumor tissue, calcifications, or markers within breast lumpectomy specimens during surgery or during a mastectomy.

Technical effects of the disclosed subject matter include providing for systems and methods for specimen imaging (e.g., intraoperative specimen imaging) utilizing an existing mammography imaging system for specimen imaging. In particular, an intraoperative specimen imaging system includes a specimen holding system configured to hold a tissue sample, wherein the specimen holding system is retrofittedly coupled to an existing mammography imaging system, wherein the intraoperative specimen imaging system is configured to acquire imaging data for generating 3D images of the tissue sample. The intraoperative specimen imaging system may be utilized within an operating room during a procedure (e.g., breast lumpectomy surgery, mastectomy, etc.) on a patient from which the tissue sample was taken to provide improved intraoperative imaging (e.g., high-resolution 3D images) at lower costs to an institution (which may not normally have intraoperative specimen imaging available).

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

This written description uses examples to disclose the present subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An intraoperative specimen imaging system, comprising:
   a mammography imaging system comprising a radiation source configured to emit radiation; and
   a specimen holding system comprising a specimen holder configured to hold a tissue sample, wherein the specimen holding system is coupled to the mammography imaging system via an attachment to form the intraoperative specimen imaging system, wherein the specimen holding system comprises a motor configured to rotate the specimen holder to rotate the tissue sample in the specimen holder to different angular positions over a specific angular range, wherein the mammography imaging system is configured to acquire imaging data at the different angular positions over the specific angular range for generating three-dimensional (3D) images of the tissue sample when radiation is emitted by the radiation source while rotating the tissue sample in the tissue holder to the different angular positions.

2. The intraoperative specimen imaging system of claim 1, wherein the mammography imaging system is configured to acquire the imaging data over an angular range that is greater than 2 degrees.

3. The intraoperative specimen imaging system of claim 1, wherein the mammography imaging system comprises a full-field digital mammography imaging system.

4. The intraoperative specimen imaging system of claim 1, wherein the mammography imaging system comprises a digital breast tomosynthesis imaging system.

5. The intraoperative specimen imaging system of claim 1, wherein the mammography imaging system comprises an optical reader, and wherein the attachment comprises a marker configured to be scanned or read by the optical reader, wherein the scanning or reading of the marker is configured to cause the mammography imaging system to automatically acquire imaging data at the different angular positions with the motor rotating the tissue sample between each angular position.

6. The intraoperative specimen imaging system of claim 1, wherein the attachment is configured to couple the specimen holding system to a portion of the mammography imaging system where a compression paddle or magnification stand is configured to couple to the mammography imaging system.

7. The intraoperative specimen imaging system of claim 1, wherein the specimen holder comprises a radio-opaque fiducial configured to provide a distance and location for the tissue sample in a subject from which the tissue sample was obtained.

8. The intraoperative specimen imaging system of claim 1, wherein the intraoperative specimen imaging system comprises processing circuitry, wherein the processing circuitry is configured to add an electronic fiducial to an image of the tissue sample subsequent to acquisition of the imaging data.

9. The intraoperative specimen imaging system of claim 2, wherein the angular range extends up to at least 360 degrees.

10. The intraoperative specimen imaging system of claim 6, wherein, when the attachment is coupled to the portion of the mammography imaging system, the mammography imaging system is configured to enter a magnification mode.

11. A method for intraoperative specimen imaging, comprising:
coupling a specimen holding system to a mammography imaging system, wherein the specimen holding system comprises a specimen holder, an attachment for coupling the specimen holder to the mammography imaging system, and a motor configured to rotate the specimen holder;
rotating the specimen holder to rotate a tissue sample in the specimen holder to different angular positions over a specific angular range;
emitting radiation from a radiation source of the mammography imaging system to acquire imaging data of the tissue sample at the different angular positions; and
generating three-dimensional (3D) images of the tissue sample from the imaging data acquired at the different angular positions over the specific angular range.

12. The method of claim 11, comprising displaying the 3D images on a screen within an operating room where a procedure is being conducted on a subject that provided the tissue sample.

13. The method of claim 11, comprising alternating over the specific angular range between:
emitting the radiation from the radiation source to acquire the imaging data; and
rotating the specimen holder to rotate the tissue sample to the different angular positions after emitting the radiation, wherein alternating between emitting the radiation and rotating the specimen holder occurs automatically in a synchronous manner.

14. The method of claim 11, wherein coupling the specimen holding system to the mammography imaging system causes the mammography system to enter a magnification mode when acquiring the imaging data.

15. The method of claim 11, comprising scanning or reading a marker on the attachment causing the mammography imaging system to automatically acquire the imaging data at the different angular positions while rotating the tissue sample between each angular position.

16. The method of claim 11, wherein the specific angular range is greater than 2 degrees.

17. The method of claim 16, wherein the specific angular range extends up to at least 360 degrees.

* * * * *